United States Patent
Flickinger et al.

(10) Patent No.: US 7,187,975 B2
(45) Date of Patent: Mar. 6, 2007

(54) CONNECTOR SYSTEMS AND METHODS FOR IMPLANTABLE LEADS

(75) Inventors: William J. Flickinger, Lino Lakes, MN (US); Gary L. Lubben, Independence, MN (US)

(73) Assignee: Medtronic, Inc., Minneapolis, MN (US)

( * ) Notice: Subject to any disclaimer, the term of this patent is extended or adjusted under 35 U.S.C. 154(b) by 348 days.

(21) Appl. No.: 10/816,711

(22) Filed: Apr. 2, 2004

(65) Prior Publication Data

US 2005/0222634 A1    Oct. 6, 2005

(51) Int. Cl.
*A61N 1/375* (2006.01)
(52) U.S. Cl. ........................................ 607/37
(58) Field of Classification Search ................ 607/37, 607/38
See application file for complete search history.

(56) References Cited

U.S. PATENT DOCUMENTS

| | | | | |
|---|---|---|---|---|
| 5,047,021 A | * | 9/1991 | Utterberg | 604/533 |
| 5,252,090 A | * | 10/1993 | Giurtino et al. | 439/441 |
| 5,257,622 A | * | 11/1993 | Hooper et al. | 607/37 |
| 5,489,225 A | * | 2/1996 | Julian | 439/837 |
| 5,651,776 A | * | 7/1997 | Appling et al. | 604/534 |
| 6,112,121 A | * | 8/2000 | Paul et al. | 607/37 |
| 6,332,633 B1 | * | 12/2001 | Fitoussi et al. | 285/332 |
| 6,755,694 B2 | | 6/2004 | Ries et al. | 439/668 |
| 6,912,423 B2 | * | 6/2005 | Ley et al. | 607/37 |
| 6,968,235 B2 | * | 11/2005 | Belden et al. | 607/60 |

FOREIGN PATENT DOCUMENTS

WO    WO 91/04069    4/1991

* cited by examiner

*Primary Examiner*—Carl Layno
*Assistant Examiner*—Brian T. Gedeon
(74) *Attorney, Agent, or Firm*—Michael C. Soldner; Carol F. Barry; Girma Wolde-Michael (57) ABSTRACT

A connector system for an implantable lead, which includes a header having a lumen for receiving the implantable lead. The lumen defines a mating surface and has an internal diameter larger than the lead to be connected therein. A collar is slidably engageable with the lead. Part of the collar is slidable into the header lumen, and part of the collar is releasably securable to the header such that the lead is retained in the lumen. The part of the collar that is slidable into the header lumen may be tapered. The tapered part of the collar and/or the mating surface may be formed of a compressible material.

32 Claims, 7 Drawing Sheets

CONNECTOR SYSTEMS AND METHODS FOR IMPLANTABLE LEADS

FIELD OF THE INVENTION

This invention relates to systems and methods for connecting an implantable lead to a control system of an implantable medical device, and more particularly to the connection of implantable cardiac pacing leads to pacemakers or other control units.

BACKGROUND OF THE INVENTION

Implantable cardioverter defibrillators (ICDs), pacemakers and other cardiac pacing devices are typically implanted in a patient transvenously. The sensing and pacing electrodes are implanted in the heart, attached to distal ends of associated leads. The leads and electrodes are typically implanted using an introducer sheath or catheter. The leads are preferably isodiametric so that they can be easily implanted using a standard introducer sheath. Once the physician has determined that the electrodes are correctly placed, and in order to test the pacing device, the leads must be connected at their proximal ends to the control system, the ICD or pacemaker, to test the overall system. This testing involves removing the sheath and positioning the device in a device pocket typically located in a pectoral region of the patient. The removal of the introducer sheath typically involves slitting of the sheath and peeling the sheath from the lead. Removing the sheath and positioning the device in the patient may at times dislodge the lead from its ideal location.

Typically, the control system includes one or more header ports into which the leads are connected. The headers each include a lumen, which has a standard inner diameter that is usually larger than the lead to be connected. In order to make a good connection with the header, the diameter of the lead must be increased. This is typically achieved using a lead having a connector permanently attached to the proximal end of the lead. Alternatively, with an isodiametric lead, an upsizing sleeve may be attached at the time of implantation of the device, using medical adhesive to secure the sleeve to the lead. The sleeve or connector is pushed into the header of the control system. Once a sleeve is attached to an isodiametric lead using adhesive, it cannot be removed therefrom.

Thus, if testing of the pacing device indicates that the electrodes must be repositioned, the introducer sheath cannot be replaced over the lead because the lead is not isodiametric due to the additional diameter of the connector or sleeve. The electrode and lead must then typically be completely removed from the patient, and a new sheath must be loaded with the lead must be inserted within the patient. Not only does this require a physician to ensure that a number of sheaths are available during the procedure in case new sheaths need to be used, but also adds to the time taken for the implantation of the pacing device, especially when the pacing location is difficult to access, which increases the time required for the implant procedure. In addition, the introduction of the medical adhesive may also add to the risk of contamination of the sterile field/environment.

SUMMARY OF THE INVENTION

According to one arrangement of the present invention, a connector for an implantable lead includes a header having a lumen for receiving the implantable lead. The lumen defines a mating surface and has an internal diameter larger than the lead to be connected therein. A collar is slidably engageable with the lead. At least a portion of the collar is slidable into the header lumen, and at least a portion of the collar is releasably securable to the header such that the lead is retained in the lumen.

Another arrangement of the invention relates to an implantable cardiac pacing device. The pacing device includes at least one implantable electrode, and at least one implantable lead. A control system including header having a lumen for receiving the implantable lead is included. The lumen defines a mating surface and has an internal diameter larger than the lead. A collar is slidably engageable with the lead. At least a portion of the collar is slidable into the header lumen, and at least a portion of the collar is releasably securable to the header such that the lead is retained in the lumen.

A further arrangement of the invention relates to a control system and connector for connection to implanted leads for controlling a medical device. The control system includes at least one header having a lumen for receiving an implantable lead. The lumen defines a mating surface and has an internal diameter larger than a lead to be connected therein. A collar is slidably engageable with the lead. At least a portion of the collar is slidable into the header lumen, and at least a portion of the collar is releasably securable to the header such that the lead is retained in the lumen.

In any of the foregoing arrangements of the invention, the mating surface and/or the collar may be formed of a compressible material. A portion of the collar may have a tapered surface for insertion into the header lumen. The header may have threads for threadably engaging the collar. The lead is preferably substantially isodiametric.

A sleeve may be included for insertion into the header lumen. The sleeve may have threads for threadably engaging the collar. The sleeve may be formed of a compressible material.

The collar may have a tapered section and a locking ring. The tapered section and the locking ring may be joined together or may be separate. The locking ring may be threaded. The locking ring may include an annular recess, with the threads being provided on the annular recess. The threads may be inwardly-directed. The collar may have a central lumen adapted to be a sliding fit on the lead.

The header may include at least one clamp extending substantially around the lumen. The clamp may form an electrical connection with the lead when the lead is inserted in the header. The collar may include an O-ring. In an example arrangement of implantable pacing device, the device may have at least two leads and at least two electrodes.

Another arrangement of the invention relates to a method of installing an implantable lead into a control device. The method involves attaching a slidably engageable collar on a free end of the lead. The free end of the lead is inserted into a header lumen of a control device. The collar is slid along the lead until it engages with the header lumen. The collar is releasably secured to the header to retain the lead in the header lumen.

At least a portion of the collar may be inserted into the header lumen. In one arrangement, at least a portion of the collar may have a tapered surface for insertion into the header lumen. At least one of a mating surface of the header lumen and the collar may be formed of a compressible material, the method including compressing the compressible material on insertion of the portion of the collar into the header lumen.

The collar may be threadably engaged with the header. A sleeve may be inserted into the header lumen, and at least a portion of the collar may be inserted into the sleeve. The sleeve may include threads, and the collar may be threadably engaged with the sleeve.

The collar may include a separate tapered section and a locking ring, with the method further including sliding the locking ring onto the free end of the lead, and inserting the tapered section into the header lumen. At least the tapered section may include a lumen for receiving the lead, with the method further including threading the free end of the lead into the lumen in the tapered section. The locking ring may be locked onto the header after the lead is inserted therein.

The method may further include testing the control device and the lead. The collar may be removed from the header and the lead may be removed from the header lumen for repositioning of the lead in the body. The lead may be reinstalled into the header after repositioning of the lead in the body.

The method may include releasably securing the collar to the header using a tool having projections for engaging corresponding indents provided in the header. At least one of the tool and the collar may produce a signal indicative of proper securement of the collar to the header, and the method may include securing the collar to the header until the signal is appreciated and then discontinuing the securement of the collar to the header.

Yet another arrangement relates to a method of implanting an electrically operated device into the body. The method includes the steps of placing an electrode attached to a first end of a lead at an operative site of the device and attaching a second end of the lead to a control system. The control system has a header including a lumen for receiving the lead. The second end of the lead is attached to the control system by attaching a slidably engageable collar on the second end of the lead. The second end of the lead is inserted into the header lumen. The collar is slid along the lead until it engages with the header lumen. The collar is releasably secured to the header to retain the lead in the header lumen.

At least a portion of the collar may be inserted into the header lumen. At least a portion of the collar may have a tapered surface for insertion into the header lumen.

At least one of a mating surface of the header lumen and the collar may be formed of a compressible material, the method including compressing the compressible material on insertion of the portion of the collar into the header lumen. This may compress the collar onto the lead to hold the lead in place. The collar may be threadably engaged with the header.

A sleeve may be inserted into the header lumen, and at least a portion of the collar may be inserted into the sleeve. The sleeve may have threads, and the collar may be threadably engaged with the sleeve.

The may have a separate tapered section and a locking ring, and the method may further include sliding the locking ring onto the free end of the lead, and inserting the tapered section into the header lumen. At least the tapered section may include a lumen for receiving the lead, and the method may involve threading the free end of the lead into the lumen in the tapered section. The locking ring may be locked onto the header after the lead is inserted therein.

The method may also include testing the control device and the lead. The collar may be removed from the header and the lead may be removed from the header lumen for repositioning of the lead. The lead may be reinstalled into the header after repositioning of the lead in the body.

The lead and electrode may be positioned in the body using an introducer sheath. The method may include the step of removing the introducer sheath from the lead prior to attachment of the second end of lead to the control system. The lead and electrode may be repositioned in the body using an introducer sheath, the method including the step of sliding the introducer sheath over the lead after removing the lead from the control system.

The method may include releasably securing the collar to the header using a tool having projections for engaging corresponding indents provided in the header. At least one of the tool and the collar may produce a signal indicative of proper securement of the collar to the header, and the method may include securing the collar to the header until the signal is appreciated and then discontinuing the securement of the collar to the header.

Another arrangement of the invention relates to a tool for installing a connector for an implantable lead. The tool includes a handle, and a head connected to the handle by a shank. The head has projections for engaging indentations on a collar of the connector for rotating the collar into engagement with a sleeve. The head also has an aperture for passage of the lead therethrough. The projections may be equiangularly spaced around the head. In one arrangement, two projections may be provided.

The tool may include a mechanism for signaling positive engagement of the collar with the sleeve. The mechanism for signaling the positive engagement of the collar with the sleeve may be a detent, an audible signal, and/or corresponding visual markings on the sleeve and the collar.

BRIEF DESCRIPTION OF THE DRAWINGS

There are shown in the drawings embodiments which are presently preferred, it being understood, however, that the invention is not limited to the precise arrangements and instrumentalities shown.

DESCRIPTION OF THE INVENTION

Referring to the drawings, connector systems and methods for implantable medical leads are described. Although the example connector systems and methods are described with reference to cardiac pacing devices, it should be appreciated that the connector systems of the invention are suitable for use with any implantable lead that may be used with, for example, cardiac pacing devices, neuro-stimulator devices, cochlear implants and other implantable hearing assistance devices, implantable vision assistance devices, urinary and other incontinence devices, drug delivery and pump systems, shunt systems, and any other implantable medical devices where control or electrical leads may need to be connected to a control device. With reference to cardiac devices, the connector systems and methods described herein may be used with any type of device, including single, dual and triple chamber systems.

Figure 1:
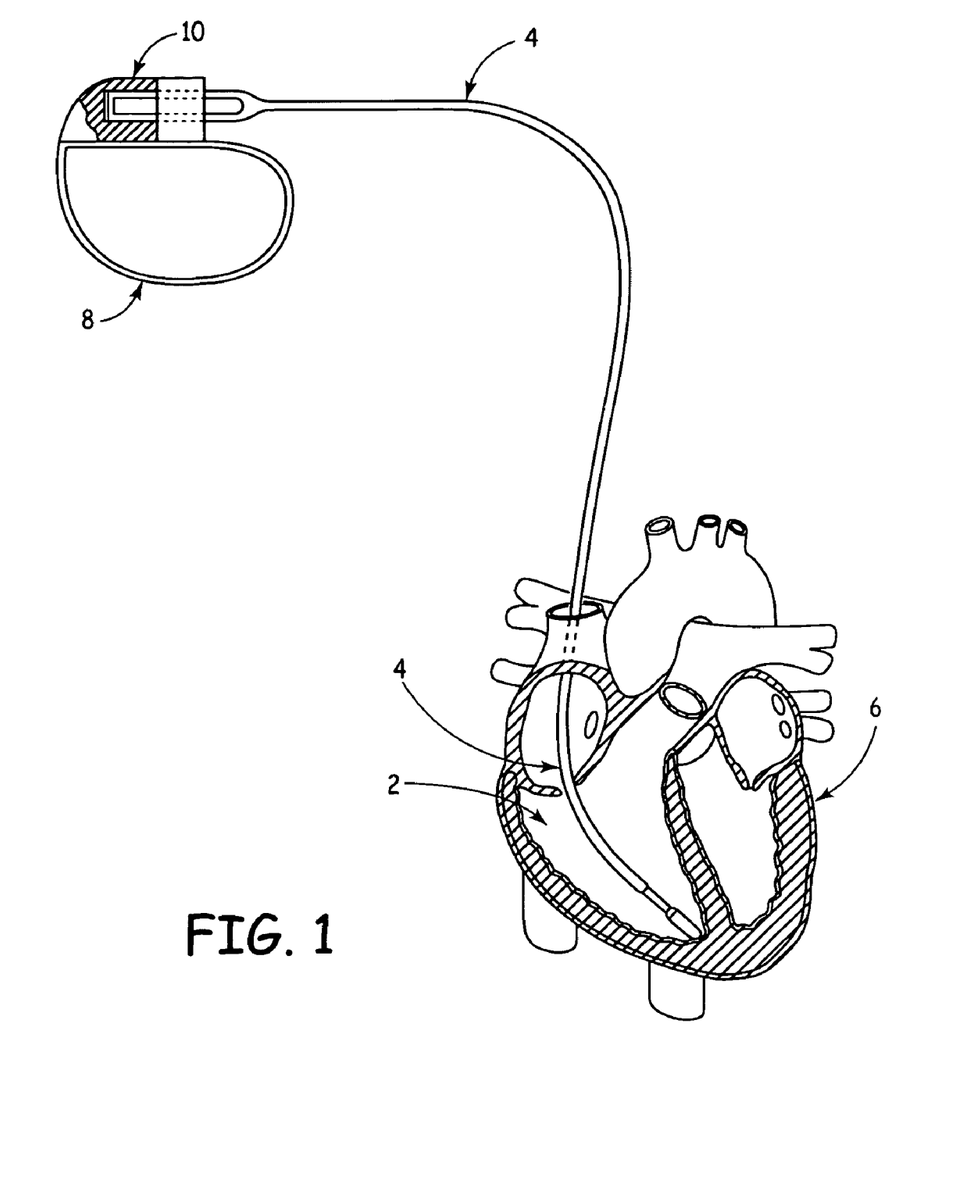
FIG. 1 is a schematic diagram of an exemplary implantable medical device in which a connector system of the present invention may be usefully practiced.

Using the example of implantation of a cardiac pacing device such as a pacemaker or implantable cardioverter-defibrillator (ICD), and referring to FIG. 1, during implantation of a cardiac pacing device, an electrode 2 located along a distal end of a lead 4 is positioned within a heart 6 transvenously or otherwise using an introducer sheath (not shown). Only one electrode 2 and lead 4 is shown in FIG. 1 for simplicity, but it will be appreciated that typically more than one lead is used in a cardiac pacing device and more than one electrode may be included along the lead. For example, one or a combination of a right ventricular lead, a coronary sinus lead, an atrial lead and a left ventricular lead may be utilized. In addition, one or more patch electrodes attached to the external heart wall may also be included either alone or in combination with other leads. When the physician believes that the electrode 2 is properly positioned with respect to the heart 6, the introducer sheath is removed from the lead 4 by sliding the sheath backwardly over the lead 4 or by slitting and peeling the sheath away from the lead using known slitting techniques. The placement of the electrode 2 and the lead 4 may be monitored using fluoroscopy or any other suitable method. The lead 4 is then attached to a housing 8 containing control circuitry for the device, and the placement and functioning of the electrode 2 is tested to ensure correct pacing and sensing prior to completion of the implantation procedure.

Referring now to FIGS. 2 through 6, an arrangement of a connector system of an implantable medical device according to the invention is illustrated. Housing 8 of the implantable medical device includes a header 10 that is integral with the housing 8 or that is part of an insert thereto. The header 10 includes lumen 12 for receiving the lead 4 that has a standard internal lumen diameter D which is larger than the diameter of the lead 4. An electrical connection (not shown) is provided in the lumen 12, or in the header 10 for forming an electrical connection between the lead 4 and the circuitry within housing 8, and could include an electrode transversing the collar or sleeve that ensures coupling between the two connections, or could include the use of multi-beam contacts, or electrically conductive collars along the length of the sleeve, and so forth.

Figure 2:
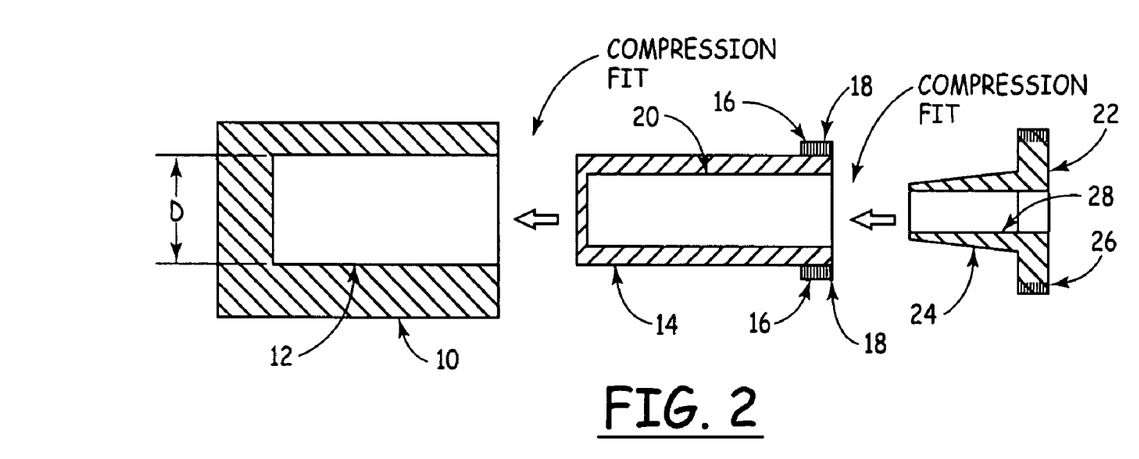
FIG. 2 is a schematic diagram of components of a connector system according to an arrangement of the invention.

A sleeve 14 may be provided, which is insertable in lumen 12. The sleeve 14 includes a lip 16 at one end thereof, the lip 16 being provided with external threads 18. The sleeve 14 also forms an internal lumen 20 sized to receive the lead 4. In the illustrated example, the internal lumen 20 is generally cylindrical in shape. The sleeve 14 may be formed of a compressible material, for example.

A collar 22 is also provided, sized to be slid over the proximal end of the lead 4. In the arrangement shown in FIG. 2, the collar 22 includes a tapered section 24 and a locking ring 26. A central lumen 28 extends through the collar 22, for sliding the collar 22 onto the lead 4. The tapered section 24 is sized for insertion of collar 22 in the lumen 20 of the sleeve 14. The tapered section 24 may be conical, and may be formed of a compressible material. It will be appreciated that the tapered section 24 need not be conical. For example, the tapered section and the sleeve lumen 20 may have complementary cross-sections, such as triangular, square, rectangular or polygonal cross-sections. The tapered section could be splined. As a further alternative, the tapered section 24 may not be tapered, but may have any suitable shape capable of exerting a fixation force on the sleeve 14. For example, a square or rectangular shaped section 24 may be twisted to cause the wider corners to exert a fixation force on a correspondingly shaped lumen 20.

As the tapered section 24 is inserted into the sleeve 14, tapered section 24 exerts a compressive force on the sleeve 14, securing the sleeve 14 into the header lumen 12, and also securing the collar 22 to the sleeve 14. If the sleeve 14 is omitted, the tapered section 24 exerts a compressive force directly on the header lumen 12. Since the tapered section 24 is formed of compressible material, the inner lumen 28 is compressed tightly onto the lead 4 as the tapered section is inserted into the sleeve 14 or header 10, which holds the lead 4 securely in place.

The locking ring 26 is arranged to lock onto the lip 16 of the sleeve 14. In the illustrated example, threads 18 are provided on the lip 16 of sleeve 14, and locking ring 26 has an annular recess including internally-directed threads (not shown) that receive and cooperate with the external threads 18 on the sleeve 14 to secure locking ring 26 onto sleeve 14. However, any suitable locking or tightening mechanism may be used.

It will be appreciated that all components of the connector system may be made of any suitable bio-compatible material, such as plastic.

Figure 3:
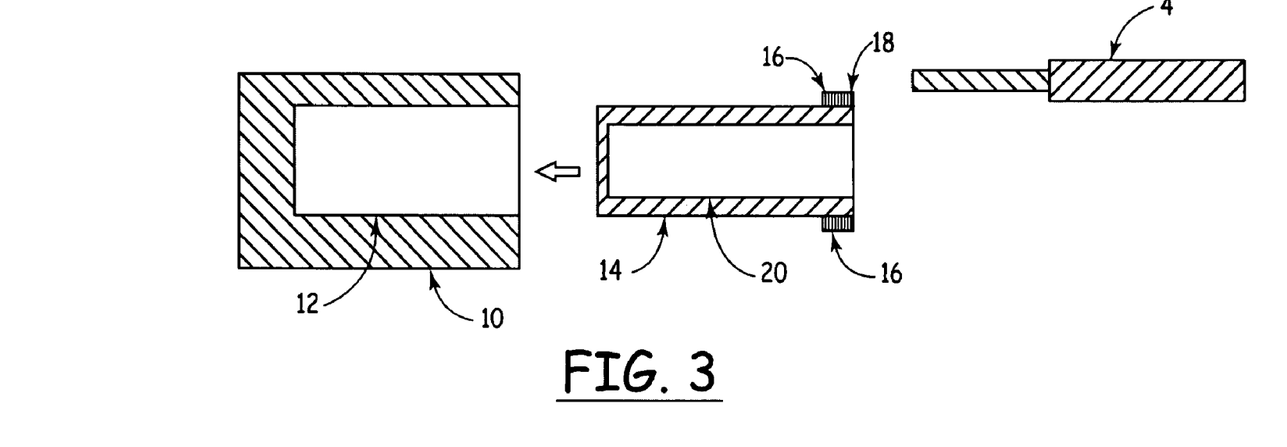
FIG. 3 is a schematic diagram of the placement of a sleeve into a header of the arrangement of the invention of FIG. 2.

A method for assembling the connector system of FIG. 2 is illustrated in FIGS. 3 through 6. Typically, the connector system will be assembled once the distal end of the lead 4 and its associated electrode 2 have been implanted in a patient using a method such as that described in relation to FIG. 1. After the placement of the lead 4, the introducer sheath is removed from the lead 4 by sliding the introducer sheath from the proximal end of the lead 4. The proximal end of the lead 4 is then available for connection to housing 8. As shown in FIG. 3, the sleeve 14 is first inserted into the lumen 12 of the header 10. The sleeve 14 may be a sliding fit into the lumen 12, and may be a friction fit therein. Alternatively, the sleeve 14 may be held in place within the lumen 12 with medical adhesive, or by any other means. The collar 22 is advanced over the proximal end of the lead 4, with the tapered section 24 of the collar 22 facing the proximal end of the lead 4, and the locking ring section 26 of the collar 22 facing the distal end of the lead 4.

Figure 4:
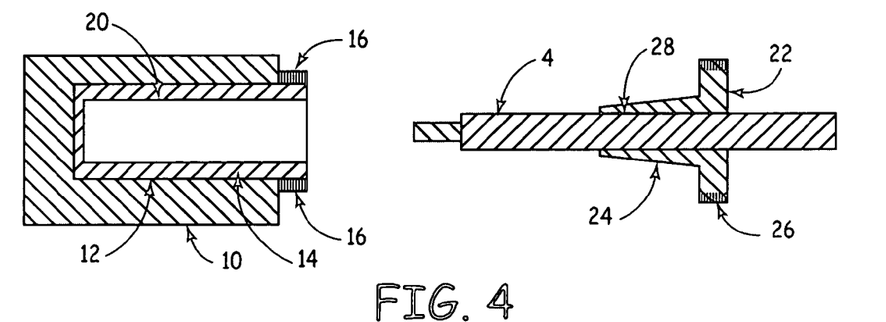
FIG. 4 is a schematic diagram of the placement of a collar on a lead of the arrangement of the invention of FIG. 2.
Figure 5:
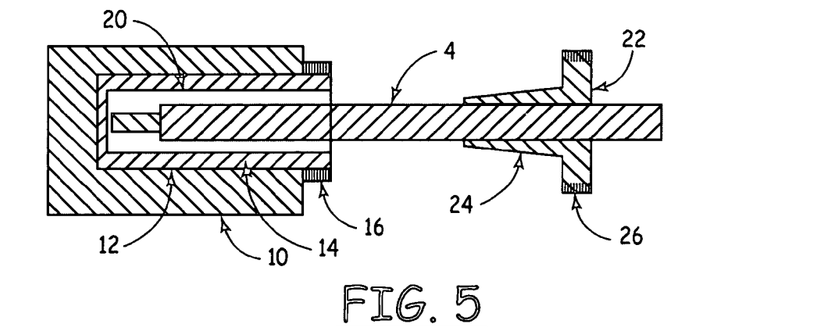
FIG. 5 is a schematic diagram of the placement of a lead into a header lumen of the arrangement of the invention of FIG. 2.

As illustrated in FIG. 4, once the collar 22 is positioned on the lead 4 bt advancing the lead 4 through the lumen 28, and sleeve 14 has been inserted within lumen 12 of header 10, the proximal end of the lead 4 is inserted into the lumen 20 of the sleeve 14 to a position enabling the connector of the lead 4 to be electrically coupled to the circuitry of the housing 8. The collar 22 is then advanced along the lead 4 until the tapered section 24 of the collar 22 engages with the lumen 20 of the sleeve 14. The collar 22 is rotated about the lead 4 so that the internally-directed threads 22 on the locking ring 26 of the collar 22 engage with the corresponding threads 18 provided on the sleeve 14. The collar 22 can be threaded onto the sleeve 14 until the collar 22 is tight. If an alternative locking mechanism is used, the collar 22 is locked onto the sleeve 14 appropriately. For example, the locking mechanism may involve a push-and-twist mechanism. In a preferred arrangement, the locking of the collar 22 to the sleeve 14 produces an appreciable signal to the physician when the collar is in the correct position. This may be achieved by means of a tactile sensation produced by, for example, a detent, an audible noise such as a click when the collar locks in position, or a visible indication such as alignment of markings on the sleeve 14 and the collar 22, or a combination of signals.

The locking of the collar 22 onto the threaded lip 16 of the sleeve 14 causes the tapered section 24 of the collar to be drawn deeper into the lumen 20 of the sleeve 14 with little or no insertion force required from the physician, as there is no need to push the tapered section 24 of the collar 22 into the lumen 20. As the tapered section 24 is drawn into the lumen 20 during the locking process, the tapered section 24 compresses the sleeve 14 slightly to form a tight fit between the sleeve 14, the header lumen 12 and the tapered section 24. Alternatively, or in addition, the tapered section 24 may be compressed slightly, which causes the tapered section 24 to grip the lead 4 securely. The placement of the tapered section 24 within the sleeve 14 causes fixation forces to develop, as illustrated by the arrows in FIG. 6, which firmly holds the lead 4 in place. In one arrangement (not shown), the collar 22 is locked on the threaded lip 16 using one or more set screws (not shown). Once the lead 4 is connected to the header 10 (and hence electrically couple to the circuitry of the housing 8), the pacing and sensing of the cardiac pacing device can be tested.

If, after testing of the cardiac pacing device in situ, it is discovered that electrode is not in an optimal position, the lead 4 can be disconnected from the housing 8 by unscrewing the collar 22 from the sleeve 14 (or otherwise unlocking the collar 22 from the sleeve 14) and removing the collar 22 from the sleeve 14. This decompresses the tapered section 24, releasing the lead 4, which enables the collar 22 to be easily removed from the lead. The lead 4 is removed from the collar 22 so as to be returned to an isodiametric condition so that the introducer sheath can be subsequently advanced over the lead 4 for repositioning of the electrode 2 by the physician. Once the positioning of the electrode 2 is completed, the introducer sheath is removed from the lead 4 again, and the lead 4 is connected to the header 10 as described above for further testing. In this way it is not necessary to insert a new lead if repositioning of a lead and its associated electrode is deemed necessary. The lead 4 may be easily repositioned in the header 10 for any other reason while minimizing damage to the lead. Repositioning in the header may be necessary, for example, if the housing device 8 is found to be faulty.

In retrofitting a patient with a new device after a cardiac pacing device has been implanted for a period of time, it is typically not desirable to remove the leads from the patient because of tissue encapsulation. With the example connector system described, the proximal ends of the leads can be removed from-the old housing, and a collar 22 is advanced over the lead ends. It may be necessary to clean the old connectors from the proximal ends of the leads 4 or even shorten the ends of the leads 4 in order to present a clean lead end. The leads 4 are then inserted within the header 10 of the newly implanted device and thereby coupled to the circuitry of the device for control of the electrodes 2.

Figure 6:
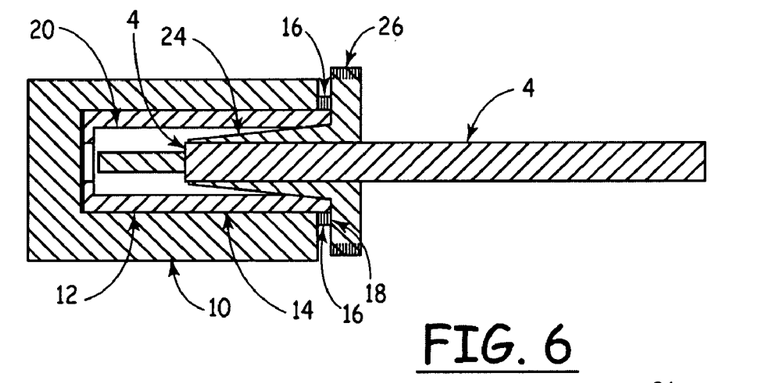
FIG. 6 is a schematic diagram of the assembled connector system of FIG. 2.
Figure 6A:
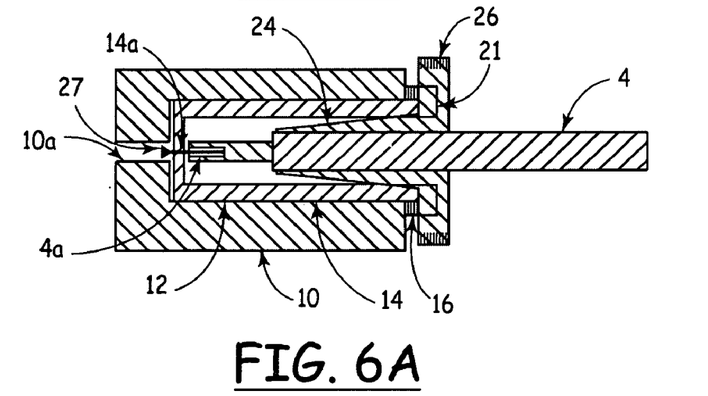
FIG. 6a is a schematic diagram of an embodiment of the assembled connector system of FIG. 6.

FIG. 6a illustrates a connector system in which a set screw 27 is threadable into a threaded bore 4a provided along the proximal end of the lead 4. The set screw 27 extends through bores 10a and 14a provided in the end of header 10 and the sleeve 14, respectively. As the set screw 27 is tightened using a suitable screwdriver (not shown), the lead 4 is pulled further into the sleeve 14, thus tightening the connection of the lead 4 to the header 10. The set screw 27 locks the lead 4 into position within header lumen 12. In an alternative arrangement, the lead 4 may be locked in place using a set screw 27 which extends through bores positioned in a side of the header 10. In this arrangement, the set screw 27 makes a compression contact point with the lead 4 to lock the lead into place.

Figure 7:
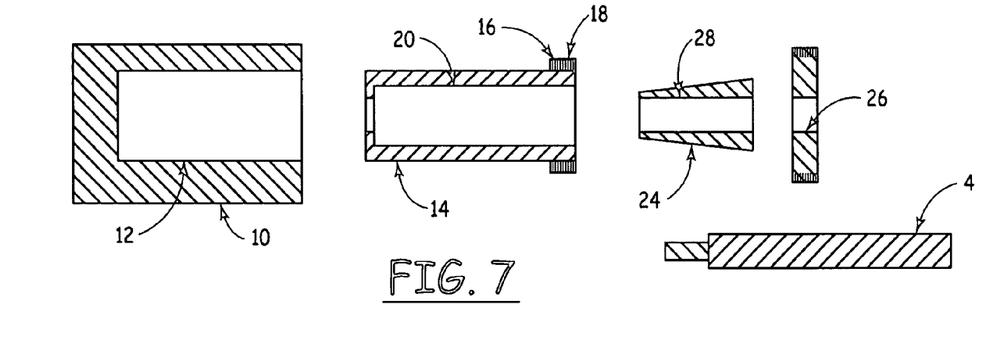
FIG. 7 is a schematic diagram of components of a connector system according to an embodiment of the invention.

FIG. 7 illustrates an embodiment of a connector system of the present invention in which the tapered section 24 and locking ring 26 of the collar 22 are separate components. This arrangement enables the tapered section 24 and the locking ring 26 to be formed of different materials. For example, the tapered section 24 may be formed of a compressible material, while the locking ring 26 may be rigid. The locking ring 26 is slid onto the lead 4, and the tapered section 24 is positioned in the sleeve 14 prior to placement of the lead 4. The lead 4 is threaded through the lumen 28 in the tapered section 26 in order to insert the lead 4 into the header 10. The locking of the locking ring 26 to the sleeve 14, as described above, causes the tapered section 24 to be drawn into the sleeve 14, which compresses the tapered section onto the lead 4 to hold the tapered section securely in place.

Figure 8:
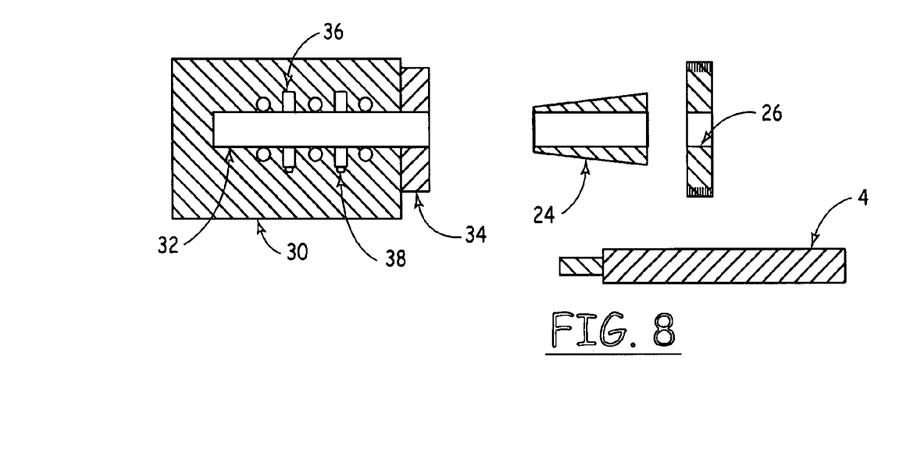
FIG. 8 is a schematic diagram of a header according to an embodiment of the invention.

FIG. 8 illustrates an embodiment of connector system according to the present invention. The tapered section 24 of collar 22 and locking ring 26 can be as described for the arrangement of FIG. 7, or the collar 22 may be provided in one piece as described for the arrangement of FIGS. 2–6, although the invention is not limited to either arrangement. The system of FIG. 8 includes a header 30 having a small-diameter internal lumen 32, and a threaded lip 34, so that the locking ring 26 of the collar 22 locks directly onto the threaded lip 34. The header 30 can be used in place of standard headers that are currently available, and is appropriate for new initial implantations.

Adjustable circumferential hose clamps 36 form sealing rings which surround the internal lumen to provide electrical isolation to the circuitry of the housing 8, either individually or in combination. For example, with a multi-polar system, the hose clamps 36 electrically isolate a single lead at a time, or all of the leads simultaneously. The hose clamps 36 are tightened using set screws 38, for example, and maintain electrical isolation across electrical connections on a multi-polar lead inside the header. The hose clamps 36 are tightened around the header lumen 32, compressing a softer material (not shown) positioned around the leads, between the electrodes. Hose clamps 36 compress a rubber, silicone or other flexible sealing material to create the seal.

Figure 9:
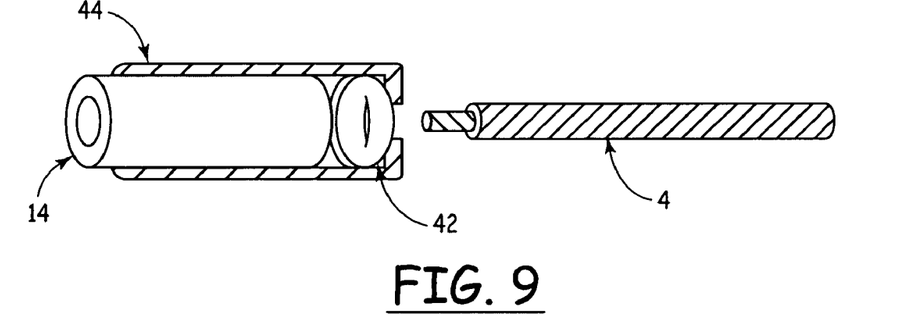
FIG. 9 is a schematic diagram of a collar and lead according to an embodiment of the invention.
Figure 10:
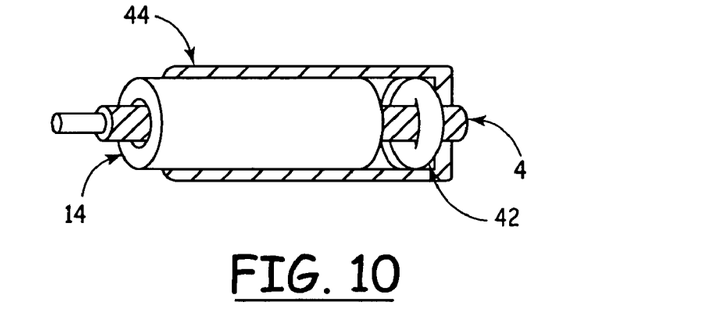
FIG. 10 is a schematic diagram of the assembled collar and lead of FIG. 9.
Figure 11:
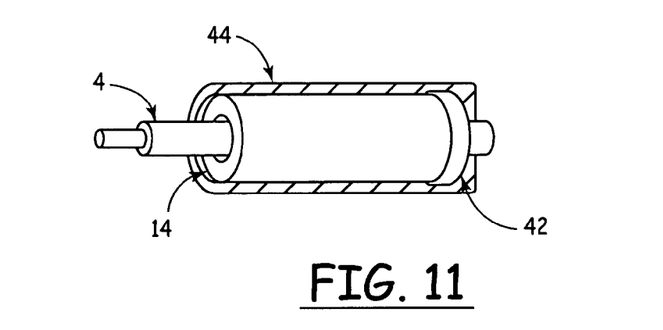
FIG. 11 is a schematic diagram of the assembled collar and lead of FIG. 9 in a compressed condition.

FIGS. 9–11 illustrate yet an embodiment of a connector system according to the present invention. A collar 40 includes a compressible O-ring type seal 42. A locking ring 44 forms part of the collar 40. The lead 4 is inserted into the O-ring 42 without interference from the locking ring 44. When the collar 40 is mated with a sleeve 14, the O-ring 42 is compressed onto the lead 4, ensuring a tight connection into the header (not shown) due to mechanical friction between the O-ring 42 and the header.

Figure 12:
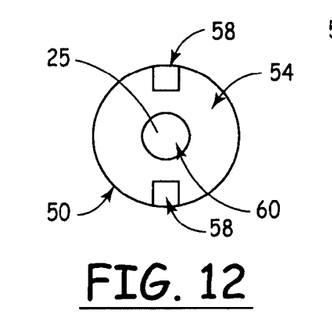
FIG. 12 is an end view of a tool according to an embodiment of the invention.
Figure 13:
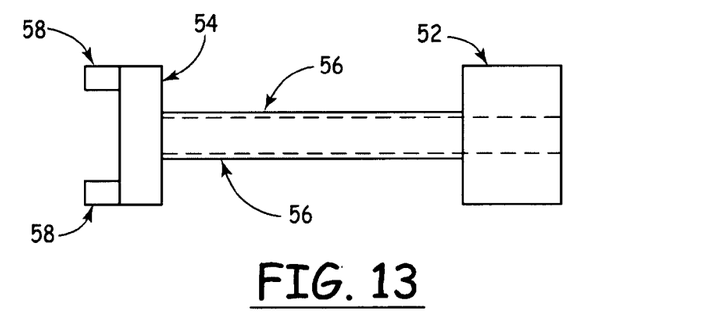
FIG. 13 is a side view of the tool of FIG. 12.

FIGS. 12 and 13 illustrate a tool 50 which can be utilized to aid in installation of a connector system of the present invention. The tool 50 includes a handle 52 and a head 54 connected by a shank 56. The handle 52 is formed in a flat paddle shape, a round knurled shape of sufficient circumference so as to aid the physician in gripping the tool, a hexagonal shape, or any other suitable shape. The head 54 is generally circular in plan view, and includes two or more equiangularly spaced projections 58. The projections 58 engage similarly positioned indents (not shown) provided in the locking ring 26 of the collar 22. The tool 50 is positionable on the locking ring 26 of the collar 22, with the lead 4 either passing between the projections 58, or through an aperture 60 in the head 54, shank 56 and handle 52. The tool 50 is used to thread the locking ring 26 of the collar 22 onto the lip 16 of the sleeve 14.

The tool 50 may include means (not shown) to give a positive indication to the physician when the collar 22 has been locked onto the sleeve 14. This is useful as the physicians are typically double-gloved, and may therefore not have enough sensation in their fingers to easily feel when the collar 22 has been properly secured onto the sleeve 14. The means for giving a positive indication include a detent that snaps into position when the collar 22 has been threaded far enough onto the sleeve 14, or may include a change in the pattern of the threads that can be felt by the physician. A further alternative is that the handle 52 of the tool may become disassociated from the head 54 when the collar 22 has been locked onto the sleeve 14. For example, the handle 52 may spin on the shank 56 once a predetermined force to turn the tool 50 has been reached. Alternatively, or in addition, an audible click or other sound may be produced when the collar 22 is locked onto the sleeve 14. Another alternative arrangement is to provide corresponding markings on the sleeve 14 and the collar 22 which may, for example, align when the collar 22 is locked onto the sleeve 14. Yet a further arrangement may involve providing a weakening in the shank 56 such that the shank 56 breaks or partially breaks when a predetermined amount of force for threading the collar 22 has been reached. Any combination of these means can be used such that two or more signaling means may be provided. It will be appreciated that any other form of signaling to a physician that the collar 22 is correctly in place may be used, and the invention is not limited to the arrangements described herein.

It should be understood that the examples and embodiments described herein are for illustrative purposes only and that various modifications or changes in light thereof will be obvious to persons skilled in the art, and that such modifications or changes are to be included within the spirit and purview of this application. Moreover, the invention can take other specific forms without departing from the spirit or essential attributes thereof.

What is claimed is:

1. A connector assembly for positioning a lead within an implantable medical device, comprising:
    a housing having a header forming a lumen for receiving the lead, the lumen defining a mating surface and having an internal diameter larger than the lead to be connected therein; and
    a collar slidably engageable with the lead,
    wherein the collar is capable of being slideably inserted within the lumen and is releasably securable to the mating surface of the header to fixedly position the lead within the lumen; and
    wherein at least one of the mating surface and the collar are formed of a compressible material.

2. The connector assembly according to claim 1, wherein the collar is formed of a compressible material such that releasably securing at least a portion of the collar into the header compresses at least said portion of the collar onto the lead to thereby retain the lead in the lumen.

3. The connector assembly according to claim 1, wherein a portion of the collar has a tapered surface for insertion into the header lumen.

4. The connector assembly according to claim 1, wherein the header has threads for threadably engaging the collar.

5. The connector assembly according to claim 1, wherein the lead is substantially isodiametric.

6. The connector assembly according to claim 1, further comprising a sleeve for insertion into the header lumen.

7. The connector assembly according to claim 6, wherein the sleeve has threads for threadably engaging the collar.

8. The connector assembly according to claim 6, wherein the sleeve is formed of a compressible material.

9. The connector assembly according to claim 6, further comprising an engaging mechanism to engage the collar, the engaging mechanism including a handle and a head connected to the handle by a shank, the head having projections for engaging indentations positioned along the collar to rotate the collar into engagement with the sleeve, and forming an aperture for passage of the lead therethrough.

10. The connector assembly according to claim 9, wherein the projections are equiangularly spaced along the head.

11. The connector assembly according to claim 9, further comprising means for signaling positive engagement of the collar with the sleeve.

12. The connector assembly according to claim 11, wherein the means for signaling the positive engagement of the collar with the sleeve is at least one of a detent, an audible signal, and corresponding visual markings on the sleeve and the collar.

13. The connector assembly according to claim 1, wherein the collar comprises a tapered section and a locking ring.

14. The connector assembly according to claim 13, wherein the locking ring is threaded.

15. The connector assembly according to claim 14, wherein the locking ring includes an annular recess, and wherein the threads are provided on the annular recess.

16. The connector assembly according to claim 15, wherein the threads are inwardly-directed.

17. The connector assembly according to claim 1, wherein the header includes at least one clamp extending substantially around the lumen.

18. The connector assembly according to claim 17, wherein the clamp forms an electrical connection with the lead when the lead is inserted in the header.

19. The connector assembly according to claim 1, wherein the collar includes an O-ring.

20. An implantable medical device, comprising:
    a housing having a header forming a lumen for receiving a lead, the lumen defining a mating surface and having an internal diameter larger than the lead to be connected therein; and
    a collar slidably engageable with the lead,
    wherein at least a portion of the collar is slidable into the header lumen, and at least a portion of the collar is releasably securable to the header such that the lead is retained in the lumen, and
    wherein at least one of the mating surface and the collar are formed of a compressible material.

21. The implantable medical device according to claim 20, wherein a portion of the collar has a tapered surface for insertion into the header lumen.

22. The implantable medical device according to claim 20, wherein the header has threads for threadably engaging the collar.

23. The implantable medical device according to claim 20, further comprising a sleeve for insertion into the header lumen.

24. The implantable medical device according to claim 23, wherein the sleeve has threads for threadably engaging the collar.

25. The implantable medical device according to claim 23, further comprising an engaging mechanism to engage the collar, the engaging mechanism including a handle and a head connected to the handle by a shank, the head having projections for engaging indentations positioned along the collar to rotate the collar into engagement with the sleeve, and forming an aperture for passage of the lead therethrough.

26. The implantable medical device according to claim 25, wherein the projections are equiangularly spaced along the head.

27. The implantable medical device according to claim 25, further comprising means for signaling positive engagement of the collar with the sleeve.

28. The implantable medical device according to claim 27, wherein the means for signaling the positive engagement of the collar with the sleeve is at least one of a detent, an audible signal, and corresponding visual markings on the sleeve and the collar.

29. The implantable medical device according to claim 20 wherein the collar comprises a tapered section and a locking ring.

30. The implantable medical device according to claim 29, wherein the locking ring is threaded.

31. The implantable medical device according to claim 30, wherein the locking ring includes an annular recess, and wherein the threads are provided on the annular recess.

32. The implantable medical device according to claim 20, wherein the collar includes an O-ring.

* * * * *